(12) United States Patent
Bourgeois et al.

(10) Patent No.: US 9,953,411 B2
(45) Date of Patent: Apr. 24, 2018

(54) METHOD FOR PROCESSING A DIGITAL IMAGE OF THE SURFACE OF A TYRE IN ORDER TO DETECT AN ANOMALY

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Steve Bourgeois, Palaiseau (FR); Régis Vinciguerra, Palaiseau (FR); Alexandre Joly, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 151 days.

(21) Appl. No.: 14/897,859

(22) PCT Filed: Jun. 11, 2014

(86) PCT No.: PCT/EP2014/062135
§ 371 (c)(1),
(2) Date: Dec. 11, 2015

(87) PCT Pub. No.: WO2014/198777
PCT Pub. Date: Dec. 18, 2014

(65) Prior Publication Data
US 2016/0133000 A1    May 12, 2016

(30) Foreign Application Priority Data

Jun. 13, 2013 (FR) .................................... 13 55503

(51) Int. Cl.
*G06T 7/00* (2017.01)
*G01B 11/22* (2006.01)
(Continued)

(52) U.S. Cl.
CPC .............. *G06T 7/001* (2013.01); *G01B 11/22* (2013.01); *G01M 17/027* (2013.01);
(Continued)

(58) Field of Classification Search
None
See application file for complete search history.

(56) References Cited

U.S. PATENT DOCUMENTS

| 4,311,044 A | 1/1982 | Marshall et al. ............... 73/146 |
| 7,257,996 B2 | 8/2007 | Hassler et al. .................. 73/146 |

(Continued)

FOREIGN PATENT DOCUMENTS

| EP | 1 750 089 A1 | 2/2007 | .............. G06T 7/00 |
| EP | 2 235 679 A2 | 10/2010 | .............. G06T 7/00 |

(Continued)

*Primary Examiner* — Kim Vu
*Assistant Examiner* — Nathan Bloom
(74) *Attorney, Agent, or Firm* — Fitzpatrick, Cella, Harper & Scinto

(57) ABSTRACT

To analyze a tire surface, a 3D elevational image is captured, which is formed of pixels representing points on the surface. Each point is assigned a grey-level value proportional to its elevation relative to a surface level. Based on the elevations in the elevational image, an orientational image is formed showing elevation gradients of the surface. In the orientational image, which is formed of pixels representing points on the surface, each point is assigned a grey-level value proportional to an angle formed with a direction given by a projection in an image plane of a non-zero norm vector substantially corresponding, at this point, to a gradient vector tangent to the surface and oriented in a direction of greatest slope. A filtered image is determined by transforming the orientational image using a filter to select areas that include structures similar to those in a reference orientational image of a blow hole.

10 Claims, 2 Drawing Sheets

(51) Int. Cl.
  *G06T 7/90* (2017.01)
  *G06T 7/11* (2017.01)
  *G01M 17/02* (2006.01)
  *G01N 21/88* (2006.01)

(52) U.S. Cl.
  CPC .............. *G06T 7/0004* (2013.01); *G06T 7/11* (2017.01); *G06T 7/90* (2017.01); *G01N 2021/8887* (2013.01); *G06T 2207/10028* (2013.01); *G06T 2207/30164* (2013.01)

(56) References Cited

U.S. PATENT DOCUMENTS

| | | | |
|---|---|---|---|
| 8,498,467 B2 | 7/2013 | Joly et al. | 382/141 |
| 9,002,063 B2 | 4/2015 | Joly et al. | 73/8 |
| 9,002,130 B2 | 4/2015 | Noyel et al. | 382/103 |
| 9,008,368 B2 | 4/2015 | Joly et al. | 73/8 |
| 9,025,853 B2 | 5/2015 | Noyel et al. | 382/103 |
| 9,123,112 B2 | 9/2015 | Vinciguerra et al. | |
| 2005/0078858 A1* | 4/2005 | Yao | G06K 9/00201 382/128 |
| 2005/0286046 A1* | 12/2005 | Hassler | G01B 11/2522 356/237.1 |
| 2006/0120591 A1* | 6/2006 | Cathier | G06K 9/4671 382/154 |
| 2013/0182962 A1* | 7/2013 | Hirakawa | G06K 9/4604 382/199 |
| 2013/0266189 A1 | 10/2013 | Vinciguerra et al. | 382/104 |
| 2014/0313303 A1* | 10/2014 | Davis | A61B 5/68 348/77 |
| 2015/0248577 A1* | 9/2015 | Goodwin | G06K 9/0063 382/103 |

FOREIGN PATENT DOCUMENTS

| | | | | |
|---|---|---|---|---|
| EP | 2 295 930 A1 | 3/2011 | | G06T 7/00 |
| FR | 2 966 956 A1 | 5/2012 | | G06T 7/00 |

* cited by examiner

S       Fig 5
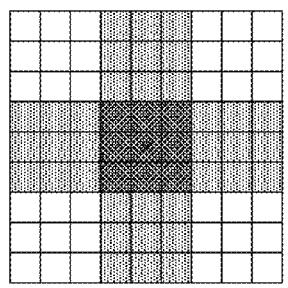
Fig 6
S
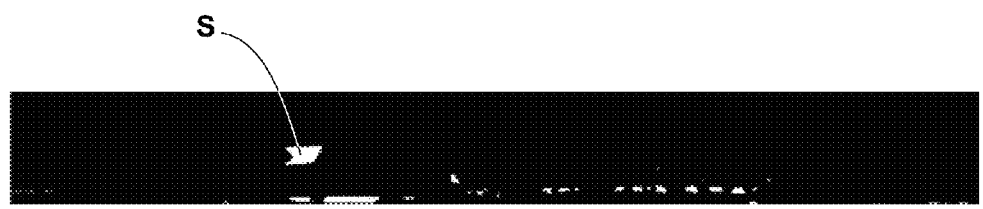
Fig 7
S
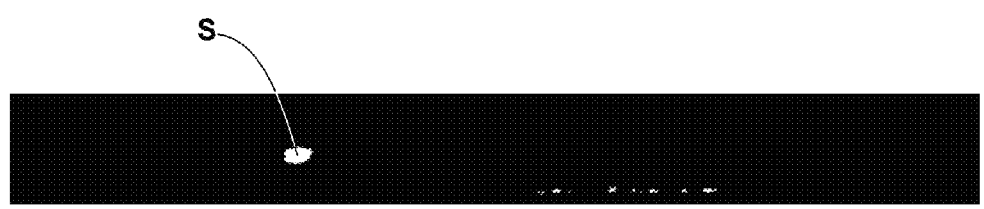
Fig 8
S
Fig 9

METHOD FOR PROCESSING A DIGITAL IMAGE OF THE SURFACE OF A TYRE IN ORDER TO DETECT AN ANOMALY

FIELD OF THE INVENTION

The invention relates to the field of tyre manufacture, and more particularly to the step in which the tyre is inspected in order to provide a diagnosis of conformity with respect to predetermined references.

RELATED ART

This step of testing can be performed by an operator conducting a detailed visual inspection of the tyre. Alternatively, automatic inspection methods are being developed, using methods for analysing an image of the tyre surface. This image may be an image of the relief, referred to as a 3D image, or an image of the colour levels, referred to as a 2D image. These two images can be used separately or can be combined, according to the specific element to be detected.

The image of the three-dimensional surface can be obtained with the aid of known means, based on the principle of optical triangulation, and using sensors coupled to light sources such as laser sources. Any other type of 3D sensor that can provide this elevation image is suitable for this method, for example sensors using stereo vision, light section, time of flight, or other techniques. In this way a topographic image of the tyre surface is obtained.

To facilitate the digital processing of the image, it is common practice to make the grey level associated with a point forming a pixel of the image correspond to the elevation of this point relative to the tyre surface. This provides a two-dimensional black and white image that can be exploited using image processing techniques adapted to the specific case of the tyre.

Among the anomalies that may appear on the inner or outer surface of the tyre, occlusions of air, causing what are generally known as blow holes, are commonly encountered.

These blow holes appear in the form of a localized swelling, forming small rises in the tyre surface level. The surface area of these blow holes rarely exceeds about ten $cm^2$, and their more or less circular shape often resembles the top of a dome. Their size rarely exceeds a few millimeters.

The geometrical characteristics of these blow holes frequently make them difficult to locate, even for experienced operators. It is therefore particularly useful to automate this task by using image processing methods such as that described in this document.

BRIEF DESCRIPTION OF EMBODIMENTS OF THE INVENTION

The invention proposes to take advantage of these dimensional characteristics. In fact, it can be seen that said blow holes have lines of greatest slope substantially converging on a centre represented by the point of greatest elevation relative to the tyre surface.

Thus the method according to the invention provides a way of capturing the three-dimensional image of the elevations of said surface and assigning to each point of the surface represented by a pixel of the image a grey level proportional to its elevation relative to said surface.

The method of analysing the resulting image is characterized in that it comprises steps in which:

- on the basis of this image of the elevations, an image of the orientation of the elevation gradients of the surface is formed, in which each point is assigned a value of grey level proportional to the angle formed with a direction given by the projection in the image plane of a non-zero norm vector substantially corresponding, at this point, to the gradient vector tangent to the surface and orientated in the direction of the greatest slope.
- a filtered image of the orientations is determined by transforming the image of the orientation of the elevation gradients using a digital filter capable of selecting the areas comprising structures similar to a reference image of the orientation of the elevation gradients of a blow hole.

As mentioned above, the image of the elevation gradients of a reference blow hole has a specific structure which is characterized in that the gradient vectors orientated in the direction of the greatest slope of the points belonging to a blow hole are all substantially orientated toward a centre corresponding to the most elevated point of said blow hole and equivalent to the top of the dome. Thus the angles formed by these gradient vectors with a given direction vary continuously from 0° to 360°. By attributing a proportional grey value to this angle, a grey variation is obtained, changing continuously along a curve at any level of the dome formed by said blow hole, the shape of which curve substantially matches the shape of a circle centred on the central point of greatest elevation. The structure of the reference image of the orientation of the elevation gradients of a blow hole therefore takes the form of a substantially circumferential gradation of grey levels.

The filtered image of the orientations is preferably obtained by finding the convolution product of the image of the orientation of the elevation gradients of the surface and a mask formed by the image of the orientation of the elevation gradients of a reference blow hole. Convolution is an operation for emphasizing the areas of the surface to be inspected in which the resemblance to this reference image is strongest.

To facilitate the calculations, the method may proceed by considering that, at each point of the image of the elevations, the gradient vector orientated in the direction of the greatest slope is equivalent to the sum of two gradient vectors tangent to the surface and orientated, respectively, in two orthogonal directions.

Preferably, a thresholding operation is performed on the filtered image of the orientations, in order to determine the areas most likely to contain a blow hole.

To reduce erroneous detections, it may be useful to provide supplementary steps in which:

- the points on the surface forming relief elements corresponding to the markings made by moulding are determined, and the grey level at these points is adjusted to the grey level of the surface to be inspected so as to obtain a corrected elevation image,
- at each point of the corrected elevation image, the mean elevations of the pixels in the near or far vicinity of the point in question are determined, and a filtered image of the elevations is determined by assigning to this pixel a grey level proportional to an elevation score calculated by comparing these mean elevations to predetermined threshold values.

The product of the filtered image of the orientations and the filtered image of the elevations can then usefully be found in order to obtain a combined image.

To improve the reading of the combined image, thresholding can be carried out on the combined image to obtain a segmented image in which the areas of the surface to be inspected which may contain a blow hole are highlighted.

BRIEF DESCRIPTION OF THE DRAWINGS

The following description is based on FIGS. 1 to 9, in which:

FIG. 5 shows the image of the surface of the tyre from which the relief elements created by the markings formed by moulding have been removed, FIG. 6 shows a schematic view of the points considered by way of example as belonging to the near or far vicinity of a point of the image, FIG. 7 shows the filtered image of the elevations of the surface, FIG. 8 shows the combined image formed by the product of the filtered image of the orientations and the filtered image of the elevations, FIG. 9 shows the segmented image after the thresholding of the combined image.

DETAILED DESCRIPTION OF EMBODIMENTS OF THE INVENTION

Figure 1:
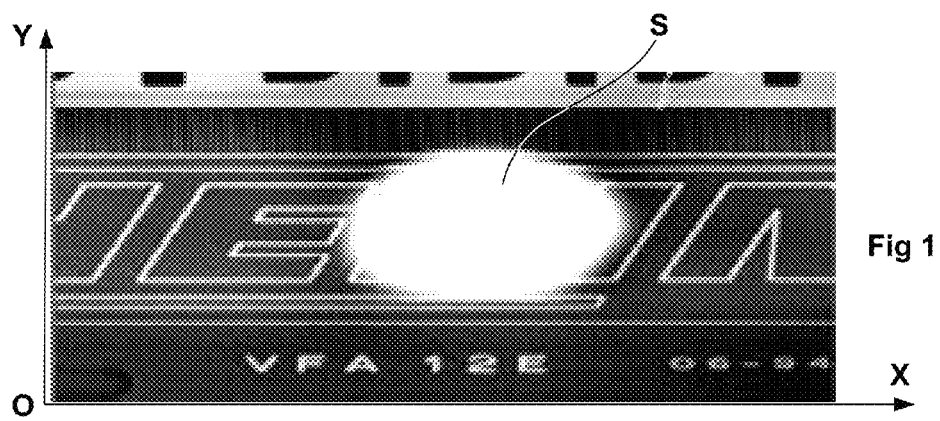
FIG. 1 shows the 3D image of the surface of a tyre.

The image of FIG. 1 shows the image of part of the surface of a tyre. It is obtained by known means for creating a three-dimensional image, these means being, for example, a 2D camera coupled to a laser lighting device emitting a radially orientated light ray at a known angle of incidence to the surface. A simple triangulation calculation can be used to find the elevation of a point relative to a reference level, here considered to be the level of the tyre surface without engraved elements.

Each point of the surface is considered to be equivalent to a pixel of the image. By assigning a low grey value (where a value of 0 corresponds to black) to the points of the surface belonging to the reference level, and a higher grey value to the relief elements (the value $2^n$, where n represents the number of bits of the acquired image, corresponding to white), it is possible to obtain an image of the surface in grey levels in which the light values correspond to the points in relief relative to the base surface, which has a darker colour.

To obtain the full image of the surface of the sidewall or of the internal part, the tyre is made to rotate about its axis. The resulting final image of the elevations is generally an image expressed in polar coordinates ($\rho$, $\theta$). For the requirements of analysis, it is therefore common practice to convert this image of the elevations to Cartesian coordinates, in which the angular values correspond to the values along a first axis (OX) and the modulus values correspond to the values along an orthogonal second axis (OY).

It should be noted that this method can be applied to the sidewall and to the interior or to any other area that may exhibit blow holes (bead, crown, shoulders, etc.). Acquisition therefore takes place on the outer and inner surfaces of the casings.

A blow hole S with a light colour, indicating its relatively elevated position with respect to the base surface, is seen to be present in the centre of the image of elevations in FIG. 1.

At this stage, the blow hole could be detected by searching for light surfaces standing out against the darker background, using a simple threshold analysis.

However, it has been found that this analysis cannot be used to filter lighter areas formed by slow changes in the altitude of the tyre surface, and caused, for example, by local deformations of the sidewall, or alternatively by relief markings with a large surface area. The invention also proposes to distinguish the blow holes from these elements.

Figure 2:
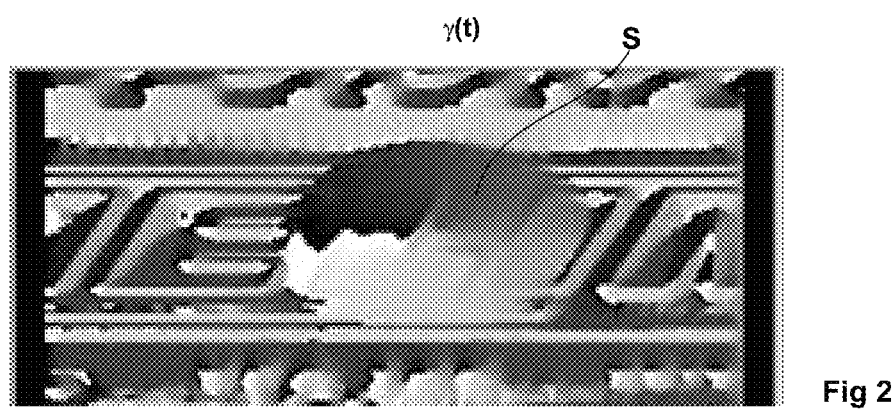
FIG. 2 shows the image of the orientation of the elevation gradients of said surface.

FIG. 2 shows the image of the orientation of the gradients of the same surface portion in which the grey level assigned to each pixel is proportional to the angle formed with the direction OX by the projection in the plane OXY of the non-zero norm gradient vector orientated, at this point, in the direction of the greatest slope.

The evaluation of the gradient having the greatest slope can be performed by successive iterations of the calculation of the derivative at the point in question, by searching for the direction in which the value of this derivative is lowest.

To simplify the calculations, this gradient is considered to be equal to the sum of the gradient vector along the direction OX and the gradient vector along the direction OY. These two vectors are tangent to the surface at the point in question, and their modulus is proportional to the elevation gradient in each of the directions OX and OY respectively.

It can then be seen that the points located at the edges of the relief marking elements have a gradient vector orientated along a direction perpendicular to the boundary line of the marking, causing these lines to show up with a grey level proportional to the angle of the line relative to the horizontal axis OX. Similarly, the variations in level due to localized radial depressions have gradient vectors orientated in the same direction, and can be recognized by the presence of dark areas in the descending part of the slope, leading toward the bottom of the depression, and light areas in the rising part of the slope.

Blow holes are characterized in that the gradient vectors orientated in the direction of the greatest slope substantially converge toward the centre of the top part of the blow hole. The angles formed with the direction OX by the gradient vectors of the points located on a circle centred on the point of greatest elevation of the blow hole therefore vary continuously from a value of 0 (corresponding to black) to a value of 360° (corresponding to white). The image of a blow hole therefore appears as a circumferential gradation of grey, as shown in FIG. 3.

It can be seen here that the blow holes may depart from the circular shape and have a shape which is more or less elongated in a given direction. However, the angles formed by the gradient vectors orientated in the direction of the greatest slope of these structures have images very similar to those of blow holes of more circular shape, in that these vectors converge toward the point of greatest elevation of the blow hole or toward a peak line which is generally of very low amplitude. They differ from them only in that the level lines are more or less elongated, resulting in a local modification of the more or less continuous variation of the grey level of the structure shown in FIG. 3.

This structure is also apparent in FIG. 2 at the location of the light area of FIG. 1, and is therefore very likely to represent a blow hole.

Figure 3:
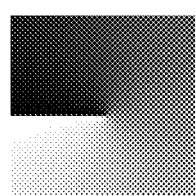
FIG. 3 shows the reference image of the orientation of the elevation gradients of a reference blow hole.

A reference image of a blow hole is therefore used to identify this area with greater certainty, by locating the areas of the image of the orientation of the gradients of the image of the tyre surface whose configuration and structure most closely resemble the structure of the image of the orientation of the gradients of greater slope of a reference blow hole such as that shown in FIG. 3.

For this purpose, use is made of a filter F, comprising a convolution operation adapted to this type of matching, and having a mask M formed by the image of the orientation of the gradients of greater slope of said blow hole.

If M denotes the model mask with a size of (2L+1)×(2H+1), O denotes the orientation image of the gradient, and ∥ ∥ denotes the angular distance, the response of the filter F characterizing the evaluated shape at the pixel (x,y) is given by:

$$F(x, y) = \frac{\sum_{i=-L}^{L} \sum_{j=-H}^{H} (D(\|O(x-i, y-j) - M(i+L, j+H)\|))}{(2L+1) \times (2H+1)}$$

with the function D defined in the following manner:
D(α)=1 if |α|≤$S_{valid}$
D(α)=0 if $S_{valid}$<|α|<$S_{error}$
D(α)=−2 if |α|≥$S_{error}$
and where $S_{valid}$ denotes the threshold below which the two pixels are considered to have a similar orientation, and $S_{error}$ denotes the threshold above which the two pixels have an orientation considered to be incompatible.

A weight can be associated with the pixels evaluated by the filter on the basis of the level of magnitude of the corresponding gradient, in order to reduce the effect of pixels having a low elevation relative to their vicinity (as the difference in elevation between a pixel and its vicinity increases, the magnitude of the gradient of this pixel also increases, and it must become more preponderant for the filter).

Figure 4:
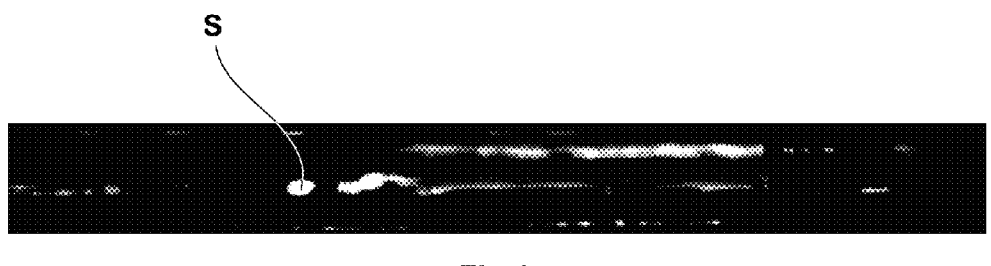
FIG. 4 shows the filtered image of the orientations of said surface.

On completion of this operation, the result is a filtered image of the orientations which can be filtered by a thresholding operation in such a way that the areas that are very likely to contain a blow hole appear in white on a black background, as shown in FIG. 4.

However, it can be seen in the image of FIG. 4 that some areas of the image appear light-coloured even though they do not contain any blow hole.

Thus, in order to eliminate these erroneously detected areas, the image of the surface can usefully be analysed by searching for the relief areas, using a different method.

For this purpose, a return is made to the image of the elevations as shown in FIG. 1, and the markings present on the surface to be inspected and produced by moulding are searched for.

There are several possible methods of detecting these points.

A first method is to use the numerical model resulting from the design data used to produce the mould. This method can be particularly successfully applied to the outer sidewalls of the tyre and to any area for which a numerical model of the relief elements can be obtained.

The method then consists of adjusting this numerical model on the surface and considering that each marking defined in the numerical model corresponds to a marking present on the sidewall of the tyre. A method of this type is described, for example, in EP 1 750 089, in EP 2 235 679, and also in FR 2 966 956.

Another possible method is that of marking the relief areas on an initial casing having no blow hole, then adjusting this map to the acquisition being analysed by conventional methods (searching for common signatures, correlation, difference minimization, etc.).

Another method is that of segmenting the image of the elevations and determining the points for which the variations of the grey gradient have a value above a certain threshold, so as to identify contours characteristic of the marking areas. It should be noted here that blow holes have much smaller elevation gradients and therefore cannot be considered equivalent to these contours.

When the points considered to belong to marking areas have been identified, the value of the grey level at these points is adjusted to the grey level of the neighbouring base surface. This operation therefore consists in eliminating the markings from the surface to be inspected in order to obtain a corrected elevation image, as shown in FIG. 5. It can also be seen here that the area where the blow hole is located forms a light area, and is therefore in relief relative to the base surface, and has not been considered equivalent to a marking area.

A search is then made for the areas in which the points/pixels show a difference in elevation, relative to their near vicinity or relative to their more distant vicinity, which lies between predetermined thresholds characteristic of the threshold values observed in commonly encountered blow holes.

The method is based on two observations:
a pixel belonging to a blow hole must have an elevation greater than a threshold $T_{High}$ relative to its vicinity, and
the probability that the pixel belongs to a blow hole is proportional to the amplitude of elevation between the centre of the blow hole and its vicinity.

To improve performance, the measurements of elevation are made by estimating the mean of the elevations along a horizontal axis OX and a vertical axis OY, without distinguishing between the different parts of the vicinity as regards importance.

Clearly, more complex measurements could be devised, by constructing a more detailed vicinity, assigning a higher or lower weight to the different areas of the vicinity in question, and choosing statistical measurements other than means.

The division of the vicinity used is shown in FIG. 6, in which the near vicinity of the point X is the vicinity shaded dark grey, and in which the more distant vicinity is indicated in lighter grey.

For a point/pixel X with coordinates (x, y) belonging to the corrected elevation image, the mean elevation is therefore measured for each of the vicinities.

These mean elevations are denoted $\mu_{proche}(X)$, $\mu_{verticale}(X)$, $\mu_{horizontale}(X)$ corresponding to the central, vertical and horizontal areas respectively.

The variation of maximum elevation is denoted $\xi_{max}$:

$\xi_{max}(X)=\max(\{\mu_{proche}(X)-\mu_{verticale}(X), \mu_{proche}(X)-\mu_{horizontale}(X), 0\}$ The variation of minimum elevation is denoted $\xi_{max}$:

$\xi_{min}(X)=\min(\max(\{\mu_{proche}(X)-\mu_{verticale}(X), 0\}), \max(\{\mu_{proche}(X)-\mu_{horizontale}(X), 0\}))$ A score ξ is assigned, corresponding to the grey level at this point, which is the result of a filter of an estimated elevation at the pixel X(x, y), and is defined as follows:

$$\xi(X) = \begin{cases} (\xi_{min}(X)/T_{Low}) & \text{if } (\xi_{max}(X) > T_{High}) \\ 0 & \text{otherwise} \end{cases}$$

where $T_{High}$ and $T_{Low}$ are two parameters of the method determined on the basis of mean values observed in blow holes commonly detected in a given range of tyres.

FIG. 7 displays the filtered image of the elevations corresponding to the result of the operations explained above.

It can be seen that the area corresponding to the blow hole highlighted by the filter of orientations and shown in FIG. 4 appears even more clearly.

Light areas not corresponding to areas that may contain blow holes are also apparent. However, these light areas are different from the light areas erroneously detected in the filtered image of the orientations of FIG. 4.

Consequently, in order to reduce the risks of erroneous detection, it may be useful to combine the results obtained with the two filters described above, by finding the product of the filtered image of the orientations as shown in FIG. 4 and the filtered image of the elevations as shown in FIG. 7, or to use any other combinatorial statistical method of combination.

In a pixel of the given image, this product is found by multiplying the value of the grey level obtained for this pixel in the filtered image of the orientations by the value of the grey level obtained for the same pixel in the filtered image of the elevations.

The result is then a combined image as illustrated in FIG. 8.

The area corresponding to the blow hole then appears distinctly.

To remove the final uncertainty caused by the filtering operations, it may be useful to perform a final filtering of the image by using thresholding, for example hysteresis thresholding.

This is a commonly used image segmentation technique which selects pixels of a grey level image on the basis of two parameters, called the high threshold (Sh) and the low threshold (Sb). The algorithm operates in the following manner:
   extract the pixels having a grey level greater than Sh=pixels P1,
   extract the pixels having a grey level between Sb and Sh=pixels P2,
   select all the pixels P1+pixels P2 connected to the pixels P1.

The end result is a segmented image in which the surface areas that may contain a blow hole appear clearly, as shown in FIG. 9. The erroneously detected areas have been entirely eliminated.

The algorithms for using the method are indicated here by way of example because of their simplicity of execution on computer equipment used in the industry. However, they may be varied in numerous ways without thereby departing from the spirit of the invention.

The invention claimed is:

1. A method for analyzing a surface of a tyre to be inspected using a three-dimensional digital image of elevations of the surface, the digital image being formed of pixels representing points of the surface, the method comprising:
   assigning to each point of the surface a grey-level value proportional to an elevation of the point relative to a surface level, to produce an elevational image formed of pixels representing the points of the surface;
   based on the elevational image, forming an orientational image of orientations of elevation gradients of the surface by assigning to each pixel of the elevational image a grey-level value proportional to an angle formed with a direction given by a projection in an image plane of a non-zero norm vector substantially corresponding, at a point represented by the pixel in question, to a gradient vector tangent to the surface, wherein each of the gradient vectors is oriented in a direction of greatest slope such that, for a blow hole on the surface of the tyre, gradient vectors corresponding to the blow hole are each oriented in a direction of greatest slope and converge toward a central top part of the blow hole; and
   determining a filtered image of the orientations by transforming the orientational image using a digital filter that selects areas including structures similar to structures in a reference orientational image of a reference blow hole, the reference orientational image showing orientations of elevation gradients of the reference blow hole having greatest slope.

2. The method of analysis according to claim 1, wherein the reference orientational image of the blow hole shows a substantially circumferential gradation of grey levels.

3. The method of analysis according to claim 1, wherein the filtered image of the orientations is determined by finding a convolution product of the orientational image and a mask formed by the reference orientational image.

4. The method of analysis according to claim 1, wherein, at each point of the surface represented by a pixel of the elevational image, the gradient vector oriented in the direction of the greatest slope is considered to be equivalent to a sum of two gradient vectors tangent to the surface and oriented, respectively, in two orthogonal directions.

5. The method of analysis according to claim 1, further comprising:
   performing a thresholding operation on the filtered image of the orientations to determine areas most likely to contain a blow hole.

6. A method for analyzing a surface of a tyre to be inspected using a three-dimensional digital image of elevations of the surface, the digital image being formed of pixels representing points of the surface, the method comprising:
   assigning to each point of the surface a grey-level value proportional to an elevation of the point relative to a surface level, to produce an elevational image formed of pixels representing the points of the surface;
   based on the elevational image, forming an orientational image of orientations of elevation gradients of the surface by assigning to each pixel of the elevational image a grey-level value proportional to an angle formed with a direction given by a projection in an image plane of a non-zero norm vector substantially corresponding, at a point represented by the pixel in question, to a gradient vector tangent to the surface and oriented in a direction of greatest slope;
   determining a filtered image of the orientations by transforming the orientational image using a digital filter that selects areas including structures similar to structures in a reference orientational image of a blow hole, the reference orientational image showing orientations of elevation gradients of the blow hole having greatest slope;
   determining relief points on the surface corresponding to relief elements of markings made by a mould, and adjusting a grey level of pixels representing the relief points to a grey level of the surface so as to obtain a corrected elevational image; and
   at each pixel of the corrected elevational image, determining mean elevations of pixels in a vicinity of the pixel in question, and determining a filtered image of the elevations of the surface by assigning to the pixel in question a grey level proportional to an elevation score calculated by comparing the mean elevations to predetermined threshold values.

7. The method of analysis according to claim 6, further comprising:
   determining a product of the filtered image of the orientations and the filtered image of the elevations to obtain a combined image.

8. The method of analysis according to claim 7, further comprising:
   performing thresholding on the combined image to obtain a segmented image showing a highlighted area, the highlighted area corresponding to an area of the surface possibly containing a blow hole.

9. The method of analysis according to claim 6, wherein the vicinity is a near vicinity.

10. The method of analysis according to claim 6, wherein the vicinity is a distant vicinity.

* * * * *

UNITED STATES PATENT AND TRADEMARK OFFICE
CERTIFICATE OF CORRECTION

PATENT NO.        : 9,953,411 B2
APPLICATION NO.   : 14/897859
DATED             : April 24, 2018
INVENTOR(S)       : Bourgeois et al.

Page 1 of 1

It is certified that error appears in the above-identified patent and that said Letters Patent is hereby corrected as shown below:

On the Title Page

Item (56), REFERENCES CITED
FOREIGN PATENT DOCUMENTS
"9,123,112 B2 9/2015 Vinciguerra et al." should read --9,123,112 B2 9/2015 Vinciguerra et al.......382/141-152--.

Signed and Sealed this
Twenty-fourth Day of July, 2018

Andrei Iancu
*Director of the United States Patent and Trademark Office*